United States Patent [19]
Shug

[11] Patent Number: 5,240,961
[45] Date of Patent: Aug. 31, 1993

[54] METHOD OF TREATING REDUCED INSULIN-LIKE GROWTH FACTOR AND BONE LOSS ASSOCIATED WITH AGING

[76] Inventor: Austin L. Shug, 5322 Lighthouse Bay Dr., Madison, Wis. 53704

[21] Appl. No.: 907,847

[22] Filed: Jul. 2, 1992

[51] Int. Cl.$^5$ .......................................... A61K 31/205
[52] U.S. Cl. .................................................. 514/556
[58] Field of Search ........................................ 514/556

[56] References Cited

U.S. PATENT DOCUMENTS

| | | | |
|---|---|---|---|
| 4,382,092 | 5/1983 | Cavazza | 514/556 |
| 5,030,458 | 7/1991 | Shug et al. | 514/556 |
| 5,104,864 | 4/1992 | DeLuca et al. | 514/167 |

FOREIGN PATENT DOCUMENTS 0126420  8/1982  Japan .................................. 514/556

OTHER PUBLICATIONS

Marcus, "Clinical Uses of Growth Hormone in Adult," Am. Soc. for Bone and Mineral Research, Clinical Day, San Diego, Calif., Aug. 28, 1991.

J. S. Johansen et al., "Insulin Like Growth Factor-1 Stimulates the Secretion of Bone GLA Protein but not the Gene Expression in Normal Adult Human Osteoblast Like Cells," Am. Soc. Bone and Mineral Res. Meeting in San Diego, Calif., Aug. 24-27, 1991. (Abstract only).

P. Ammann et al., "Chronic Infusion of IGF-1 Increases Bone Mineral Density (BMD) Evaluated Sequentially by Dual Energy X-Ray Absorptiometry (DXA) in Ovariectomized (OVX) Osteopenic Rats," Am. Soc. Bone and Mineral Res. Meeting in San Diego, Calif., Aug. 24-27, 1991. (Abstract only).

D. N. Kalu et al., "Insulin-Like Growth Factor-1 Partially Prevents Ovariectomy-Induced Bone Loss: A Comparative Study with Human Parathyroid Hormone (1-38)," Am. Soc. Bone and Mineral Res. Meeting in San Diego, Calif., Aug. 24-27, 1991. (Abstract only).

K. Mueller et al., "Insulin-Like Growth Factor-1 Increases Trabecular Bone Mass in the Ovariectomized Rat," Am. Soc. Bone and Mineral Res. Meeting in San Diego, Calif., Aug. 24-27, 1991. (Abstract only).

S. Ljunghall et al., "Is Circulating IGF-1 a Determinant for Male Osteoporosis?" Am. Soc. Bone and Mineral Res. Meeting in San Diego, Calif., Aug. 24-27, 1991. (Abstract only).

Berne, Robert, "The Endocrine System," *Physiology*, 2nd ed., (1988) pp. 878-879.

Chenu et al., *Bone*, vol. 11 (1990) pp. 81-86.

Hock et al., *Endocrinol.*, vol. 122 (1988) pp. 254-260.

Pun et al., *Bone*, vol. 11 (1990) pp. 397-400.

"Diabetes Mellitus" pp. 1-12, *Scientific American Medical Information Text*, Eds. E. Rubinstein and D. Fedman, Scientific American Soc. (1992).

Hansford et al., *Mechanisms of Aging and Dev.*, vol. 19 (1982) pp. 191-201.

Winter et al., *Am. J. Dis. Child.*, vol. 141 (1987) pp. 660-665.

*Nutr. Rev.*, vol. 36 (1978) pp. 305-309.

Chen et al., *Can. J. Chem.*, vol. 54 (1976) pp. 3310-3311.

Welling et al., *Int. J. Clin. Pharm. Biopharm.*, vol. 17 (1979) pp. 56-60.

Parvin et al., *Anal. Biochem.*, vol. 79 (1977) pp. 190-201.

Grundberg et al., *Meth. Enzymology*, vol. 107 (1984) 516-544.

(List continued on next page.)

*Primary Examiner*—S. J. Friedman
*Assistant Examiner*—William Jarvis
*Attorney, Agent, or Firm*—Stroud, Stroud, Willink, Thompson & Howard

[57] ABSTRACT

Methods of treating reduced insulin-like growth factor levels and bone loss associated with aging which include administering L-carnitine and/or its precursors thereof are disclosed. Such administration results in increased serum insulin-like growth factor-1 and osteocalcin levels.

13 Claims, 1 Drawing Sheet

OTHER PUBLICATIONS

"Normal Carnitine Levels in Body Fluids and Tissues," Metabolic Analysis Labs, Inc., Madison, Wis.

Power et al., "Osteocalcin Concentrations in Plasma Prepared with Different Anticoagulants," *Clin. Chem.*, vol. 37 (1991) pp. 281–284.

Vance, "Growth Hormone for the Elderly?" *New England Journal of Medicine*, vol. 323 (1990) pp. 52–54.

Rudman et al., *New England Journal of Medicine*, vol. 323 (1990) pp. 1–5.

Salomon et al., *N. Engl. J. Med.*, vol. 321 (1989) pp. 1797–1803.

Cuneo et al., *J. Appl. Physiol.*, vol. 70 (1991) pp. 688–700.

Marcus et al., *J. Clin. Endocrinol. Metab.*, vol. 70 (1990) pp. 519–527.

Brixen et al., *J. Bone Min. Res.*, vol. 5 (1990) pp. 609–618. (Abstract only.).

Stracke et al., *Acta Endocrinol.*, vol. 107 (1984) pp. 16–24.

METHOD OF TREATING REDUCED INSULIN-LIKE GROWTH FACTOR AND BONE LOSS ASSOCIATED WITH AGING

TECHNICAL FIELD

This invention relates generally to methods of improving aging phenomena, in particular, to a method of stimulating formation of insulin-like growth factor, and preventing bone loss, by administering L-carnitine and/or carnitine precursors to patients. The invention is particularly well-suited for administration to the elderly who generally suffer from decreased insulin-like growth factor levels as well as bone loss and muscle weakness.

BACKGROUND OF THE INVENTION

In middle and late adulthood, all people experience a series of progressive alterations in body composition. The lean body mass shrinks and the mass of adipose tissue expands. The contraction in lean body mass reflects atrophic processes in skeletal muscle, liver, kidney, spleen, skin and bone.

These structural changes have been considered unavoidable results of the aging process. It has recently been proposed, however, that reduced availability of growth hormone in late adulthood may contribute to such changes. For example, after about the age of 30, the secretion of growth hormone by the pituitary gland tends to decline.

Pituitary growth hormone is a classical endocrine hormone which has profound effects on somatic growth and body composition. Growth hormone secretion is both pulsatile and diurnal. It is, thus, difficult to measure the 24-hour secretion of the hormone directly.

Growth hormone secretion, however, can be measured indirectly by measuring the serum concentration of insulin-like growth factor 1 (IGF-1; also known as somatomedin C) which is produced and released by the liver and perhaps other tissues in response to growth hormone, and which serves as an indicator of overall growth hormone secretion. Serum IGF-1 concentrations increase in response to both endogenously and exogenously administered growth hormone, have little diurnal variation, and are low in the case of growth hormone deficiency. Serum IGF-1 concentrations also decline with advancing age in healthy adults. Less than five percent of healthy men 20 to 40 years old have serum IGF-1 values below 350 U per liter (1 unit=240 ng); however, 30 percent of healthy men over 60 have values below this figure. Decline, with advanced age, of serum IFG-1 concentration has been correlated with the decline or disappearance of the nocturnal pulses of growth hormone secretion. If the serum concentration of IGF-1 falls below about 350 U per liter in older adults, no spontaneous circulating pulses of growth hormone can be detected by currently available radioimmunoassay methods. The concomitant decline in serum concentrations of both hormones supports the view that the decrease in IGF-1 results from diminished growth hormone secretion. At all ages, it has been found that serum level of IGF-1 is inversely correlated with adiposity.

Diminished secretion of growth hormone is accompanied not only by a fall in the serum IGF-1 concentration, but also by atrophy of the lean body mass and expansion of the mass of adipose tissue. These alterations in body composition caused by growth hormone deficiency can be reversed by replacement doses of the hormone, as shown by experiments in rodents, children and adults 20 to 50 years old. These findings suggest that the atrophy of the lean body mass and its component organs and the enlargement of the mass of adipose tissue that are characteristic of the elderly result, at least, in part, from diminished secretion of growth hormone. If so, age-related changes in the body composition should be correctable, in part, by the administration of human growth hormone, now readily available as a biosynthetic product. Several studies have now confirmed that beneficial results can be obtained from growth hormone treatment. See, for example, Rudman et al., *New England Journal of Medicine*, vol. 323 (1990) pp. 1-5, in which healthy aged men who had IGF-1 levels below 350 U/L were administered growth hormone. See, also, Salomon et al., *N. Engl. J. Med.*, vol. 321 (1989) pp. 1797-1803; Cuneo et al., *J. Appl. Physiol.*, vol. 70 (1991) pp. 688-694; Cuneo et al., *J. Appl. Physiol.*, vol. 70 (1991) pp. 695-700 et al *J. Clin. Endocrinol. Metab.*, vol. 70 (1990) pp. 519-527.

Much of the focus of such studies has centered on changes in muscle and bone associated with growth hormone levels. See, for example, Brixen et al., *J. Bone Min. Res.*, vol. 5 (1990) pp. 609-618; Stracke et al., *Acta Endocrinol.*, vol. 107 (1984) pp. 16-24; Chenu et al., *Bone*, vol. 11 (1990) pp. 81-86. At least one study suggests that IGF-1 itself has an independent effect on bone matrix formation; see, Hock et al., *Endocrinol.*, vol. 122 (1988) pp. 254-260. It has been found that some bone deterioration associated with age, e.g., kyphosis, is irreversible, thus supporting a view that growth hormone might be beneficially used as a prophylactic.

One marker of bone remodeling/formation is the serum level of osteocalcin, a vitamin-K dependent protein synthesized in bone. Pun et al., *Bone*, , vol. 11 (1990) pp. 397-400. Measurement of circulating levels of osteocalcin can provide information on bone turnover. The Pun et al. study found a significant correlation between serum osteocalcin levels and IGF-1, indicating that IGF-1 is a determinant of serum osteocalcin.

While studies suggest potential benefits to body composition of growth hormone administration, some serious concerns remain regarding the effects of long term administration of growth hormone. Numerous studies suggest both beneficial and harmful effects on metabolic function. Toxic, or potentially toxic, side-effects of prolonged growth hormone treatment (i.e., daily administration over several weeks' time) which have been observed with the administration of moderate or high doses (i.e., doses above normal blood levels) include stimulation of neoplastic growth, acromegaly, amenorrhea, flushing and nausea, "dawn" phenomena (a condition of insulin insufficiency which is very dangerous for diabetics), either hyperglycemia or hypoglycemia in diabetics, and fluid retention caused by kidney glomeruli retention of sodium. (*Scientific American Medical Information Text*, Eds. E. Rubinstein and D. Fedman, Scientific American Soc. (1992)) Thus, similar to treatment with other hormones, long-term use is often a balancing act.

Moreover, efforts to administer IGF-1 rather than growth hormone have also raised concerns of harmful effects. Potential side-effects of prolonged (as defined above for growth hormone) treatment with moderate or high doses (as defined above for growth hormone) of IGF-1 include abdominal bloating, indigestion and nausea, and alteration in cellular insulin receptor sites. The latter effect could result in changes in glucose or fatty acid oxidation, as well as either insulin insufficiency or excess. Such effects are quite dangerous for diabetics. (*Scientific American Medical Information. Text*, Eds. E. Rubinstein and D. Fedman, Scientific American Society (1992))

In addition to diminished growth hormone levels with increasing age, other studies have reported age-linked changes in the activity of enzymes and cofactors involved, for example, in the tricarboxylate cycle and lipid oxidation. One such cofactor is carnitine ($\beta$-hydroxy-$\gamma$-N-trimethylammounium butyrate). Carnitine is required for fatty acid oxidation a major source of energy for normal body function. Carnitine has two critical functions in the cell, namely, (1) to stimulate fatty acid oxidation by transporting acyl groups across the inner mitochondrial membrane, resulting in ATP formation, and (2) to remove extra or "toxic" acyl groups from the mitochondria and cell as carnitine esters.

Carnitine is present in both serum and urine in free and esterified forms, although in human beings carnitine esters are preferentially excreted while free carnitine is reabsorbed by the kidney. Normal total serum carnitine concentrations range from 31–79 $\mu$M for men and 25–69 $\mu$M for women, and free carnitine from 28–68 $\mu$M for men and 21–57 $\mu$M for women. Carnitine deficiency is defined as a total serum carnitine of 20 $\mu$M or lower, or a free carnitine of 20 $\mu$M or lower. The ratio of esterified carnitine, i.e., carnitine esters, to free carnitine, E/F, is a relatively good indicator of mitochondrial oxidation and ATP formation. An E/F ratio of 0.4 or higher is indicative of free carnitine insufficiency and indicates poor oxidation of fatty acids and low ATP production. An abnormally high E/F ratio may also indicate increased removal of toxic acyl groups because of a genetic enzyme defect, ingestion of potentially toxic compounds (e.g., valproic acid), or a generalized decrease in carnitine-related metabolism associated with, e.g., aging. Related animal studies have indicated that both lipid oxidation and carnitine levels are decreased in aged rats. (Hansford et al., *Mechanisms of Aging and Dev.*, vol. 19 (1982) pp. 191–201.)

Carnitine has also been shown to be important in normal growth. (S. C. Winter et al., *Am. J. Dis. Child.* vol. 141 (1987) p. 660) For example, children with carnitine deficiency have stunted growth which normalizes with carnitine repletion.

Thus, the prior art teaches age-linked decreases in body levels of growth hormone. The prior art also teaches the use of growth hormone to retard bone loss associated with aging, and that IGF-1 concentration serves as an indicator for overall growth hormone secretion and that osteocalcin concentration is an indicator of bone formation. The art has, however, not provided any link between in vivo carnitine level and IGF-1 or bone loss.

SUMMARY OF THE INVENTION

The present invention provides a method for treating reduced insulin-like growth factor levels, and bone loss associated with aging, with L-carnitine and precursors thereof as defined in formula (I) hereinbelow. With the exception of the data provided herein, no clinical data are available which correlate administration of L-carnitine or its precursors with improvement in IGF-1 levels and improved bone formation.

It has now been found unexpectedly that compounds of formula (I) administered to animals and human beings provide surprising improvements in serum IGF-1 levels of these subjects; such improvements ar suggestive of improved growth hormone levels. As explained in detail hereinbelow, a random selection of patients over 60 years of age, only one of whom had a pretreatment IGF-1 level of less than 350 U/L (the criterium for low growth hormone level for the Rudman et al. study described hereinabove), administered L-carnitine showed increased IGF-1 levels above 500 U/L. It has also been unexpectedly discovered that such administration to human beings additionally has the advantageous effect of increasing serum osteocalcin levels. The administration of compounds of formula (I) has further been shown to be accompanied by an increase in vertebral bone mineral content. Thus, the present invention provides novel methods and compositions for chemical or biochemical events that lead to elevated IGF-1 levels, suggestive of improved growth hormone levels, and elevated osteocalcin levels, indicative of bone formation. In these methods and with these compositions, these levels are improved by virtue of an increased carnitine level.

The foregoing, and other advantages of the present invention, are realized in one aspect thereof in a method for stimulating the production of insulin-like growth factor by administering an effective amount of a compound of formula (I). The compound of formula (I) is administered in a daily dose of about 1.5 g to about 5 g, preferably about 2 g to about 4 g.

In another aspect, the invention provides a method for stimulating bone formation by administering an effective amount of a compound of formula (I).

In still another aspect, the present invention provides a method for increasing bone mineral content in a patient having an elevated serum ratio of esterified carnitine to free carnitine comprising administering an amount of the compound of formula (I) effective to normalize free carnitine serum level. In still other aspects, the invention is a method of preventing bone loss or bone demineralization by administering a compound of formula (I) in an amount effective to increase serum IGF-1 concentration or to increase serum osteocalcin concentration.

The compound of formula (I) is provided in pharmaceutical compositions, comprising an amount effective to increase serum IFG-1 concentration or to increase serum osteocalcin concentration, in combination with a physiologically acceptable vehicle. These compositions constitute another aspect of the invention. Preferred in a pharmaceutical composition are compounds of formula (I) which include L-carnitine and $\gamma$-butyrobetaine (a carnitine precursor as explained hereinbelow) or a combination of the foregoing.

Other advantages and a fuller appreciation of the specific adaptation, compositional variations and physical attributes of this invention will be gained upon an examination of the detailed description of preferred embodiments, taken in conjunction with the appended drawing and claims.

BRIEF DESCRIPTION OF THE DRAWING

The preferred exemplary embodiments of the present invention will hereinafter be described in conjunction with the appended drawing, wherein.

DETAILED DESCRIPTION

Figure 1:
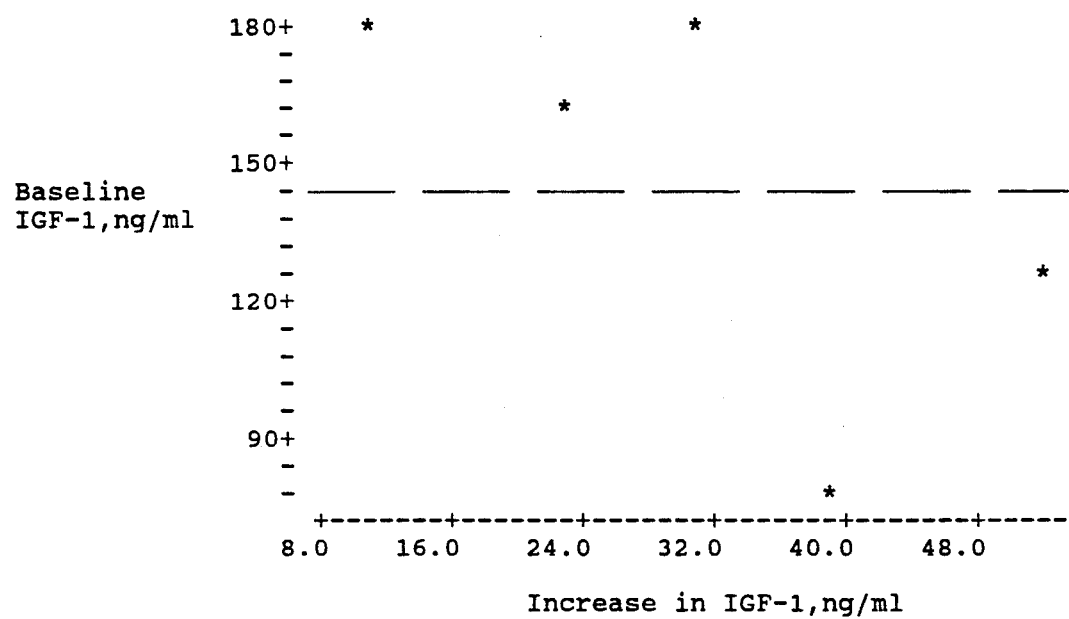
FIG. 1 is a graphical representation of the relationship between baseline (pretreatment) serum IGF-1 levels and increase in IGF-1 levels after L-carnitine treatment.

The present invention relates broadly to methods for ameliorating the effects on the body associated with aging, and specifically to a method for treating an aged animal subject, including human subject, which effects elevated levels of IGF-1 and osteocalcin in the subject, the reduction of which are associated with the aging process. These attributes are achieved through a novel treatment of the subject with the compounds of formula (I) defined hereinbelow, namely, L-carnitine and γ-butyrobetaine.

The present invention is intended for use in all subjects who exhibit aged-linked changes in growth hormone and bone depletion, and who exhibit an elevated serum ratio of esterified carnitine to free carnitine. The present invention is also intended for use to stimulate serum osteocalcin concentration, indicative of bone formation, and as a prophylactic agent to prevent bone loss.

As used herein, the term "aged" is meant to designate in mice, those which are at least 18 months old, and in human beings, those who are 45 years old or over. As used herein and generally in the art, the term "inner salt" refers to the fact that a molecule possess both a positive and negative charge, i.e., one part of the molecule functions as a cation while another part of the molecule acts as an anion.

In one of its aspects, the invention is a method for stimulating the production of insulin-like growth factor which comprises administering to a subject an effective amount of a compound of formula (I):

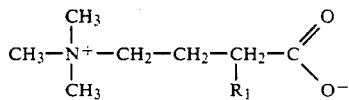

wherein $R_1$ is hydrogen or hydroxyl. While the compounds of formula (I) are illustrated as inner salts, alternative forms such as the protonated carboxylate group, that is, e.g., a hydrochloride, are considered within the scope of the present invention. When $R_1$ is hydrogen, the compound is 4-trimethylamino butyrate, also known as γ-butyrobetaine; when $R_1$ is hydroxyl, the compound is L-carnitine. Preferred embodiments include γ-butyrobetaine, L-carnitine or a combination thereof. The effective amount is suitably an amount effective to increase serum IFG-1 concentration in the subject.

It is noted that γ-butyrobetaine is the precursor of L-carnitine in the biosynthetic pathway of the latter compound (*Nutr. Rev.*, vol. 36 (1978) pp.305-309) and has been described as useful in certain carnitine deficiency states. The present inventor's U.S. Pat. No. 5,030,458 describes use of γ-butyrobetaine as a prophylactic agent for diet-induced carnitine deficiency in dogs and cats. U.S. Pat. No. 4,382,092 to Cavazza discloses use of γ-butyrobetaine to alleviate carnitine deficiency syndromes in humans beings.

Bone formation can also be stimulated by administering an effective amount of a compound of formula (I). The effective amount is suitably an amount which increases serum osteocalcin concentration and stimulates bone formation. This method constitutes another aspect of the invention.

The compounds of formula (I) have been found to possess valuable biological activity, acting as stimulants to insulin-like growth factor production and bone formation, as manifest by increasing serum levels of IGF-1 and osteocalcin, respectively. The compounds of formula (I) are water soluble, permitting ease of use by all means of drug delivery systems. The inner salt embodiment of formula (I) is particularly advantageous as it is readily soluble in water and dissolution provides a neutral solution of virtually physiologic pH. The compounds are commercially available from, e.g., Sigma Tau Chemical Co., Rome, Italy; Sigma-Aldrich Chemical Co., St. Louis, Mo.; and a method of preparing γ-butyrobetaine is described in *Can. J. Chem.* vol. 54 (1976) pp. 3310–3311.

The compounds of formula (I) have very low toxicity, which enhances their pharmaceutical properties. Compounds of formula (I) have a toxicity, as measured by the $LD_{50}$ test, which is about twice that of sodium chloride, i.e., they are half as toxic as ordinary table salt.

The compounds of formula (I) are useful as active compounds in pharmaceutical compositions having reduced side effects and low toxicity. Such compositions may include physiologically acceptable vehicles or carriers. These pharmaceutical compositions constitute another aspect of the invention.

The pharmacologically active compounds of this invention can be processed in accordance with conventional methods of pharmacy to produce medicinal agents for administration to patients, e.g., mammals including human beings. For example, the compounds of formula (I) can be employed in admixtures with conventional excipients, e.g., pharmaceutically acceptable carriers suitable for enteral (e.g., oral), parenteral, or topical application which do not deleteriously react with the active compounds.

Suitable pharmaceutically acceptable carriers include, but are not limited to, water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, can be mixed with auxiliary agents, e.g., lubricants, preservatives, stabilizers, wetting agents, emulsifiers, salts for influencing osmotic pressure, buffers, coloring, flavoring and/or one or more other active compounds, for example, hormones, such as estrogens, vitamins, and other agents which have been shown to stimulate bone formation or prevent bone deterioration in individuals experiencing or tending toward bone loss or bone demineralization. A preferred preparation is a combination of a compound of the present invention and 1α-hydroxy vitamin $D_2$, a compound which has been recently shown to exhibit low toxicity compared to other vitamin D analogues and which can be administered in sufficient doses to promote bone formation (see. U.S. Pat. No. 5,104,864, issued to DeLuca et al.). Another preferred preparation is a combination of a compound of the present invention and estrogen. Estrogens are known to be helpful in preventing certain bone deterioration associated with aging in women.

For enteral application, particularly suitable are tablets, dragees, drops, lozenges, powders, suppositories or capsules with, e.g., talc or a hydrocarbon excipient or binder such as lactose, cornstarch or potato starch. Use can also be in liquid form, e.g., as syrup, elixir, or the like to which a sweetener is added, if desired.

Oral administration of the pharmaceutical compositions of the present invention is preferred. Generally, the compounds of this invention are dispensed by unit dosage form comprising about 0.25 g to about 1.25 g in a pharmaceutically acceptable vehicle. The daily dosage of the compounds in accordance with the invention generally is about 1 g to about 5 g, preferably about 2 g to about 4 g orally. Because the serum half-life of carnitine in human beings is about 30 minutes (P. G. Welling et al., *Int. J. Clin. Pharm. Biopharm.*, vol. 17 (1979) pp. 56-60), it is preferred that the daily dosage be divided into separate unit dosages administered separately, e.g., four separate unit dosages administered four times daily.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, body weight, general state of health, sex, on the diet, on the timing and mode of administration, on the rate of excretion, on medicaments used in combination, and on the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

The compounds in accordance with the present invention can also be used in veterinary medicine. The compounds are generally administered to animals, including, but not limited to, mammals, specifically, rodents, dogs, cats, to increase osteocalcin levels. The daily dosage of the compounds of formula (I) is about 25 mg/kg to about 100 mg/kg of animal body weight.

The present invention is further explained by the following examples which should not be construed by way of limiting the scope of the present invention. In the following examples, serum carnitine levels were determined by the method of R. Parvin et al., *Anal. Biochem.*, vol. 79 (1979) pp. 190-201. Serum IGF-1 concentrations were measured by immunoradiometric assay, for example, by IRMA Kit available from Diagnostic Systems Laboratories, Inc., Webster, Texas. Serum osteocalcin levels were measured according to the method of Grunaberg et al., *Meth. Enzymology*, vol 107 (1984) 516, and which is embodied in an osteocalcin kit available from Biomedical Technologies, Inc., Stoughton, Mass. All mice used in the animal studies were BALB/c strain which is commercially available.

ANIMAL STUDIES

EXAMPLE 1

Osteocalcin response to L-carnitine in aged mice (18 months old) and young mice (3-5 months old)

Forty aged mice were separated into two groups. After an initial acclimatizing period of one week, one group was fed a diet with L-carnitine supplementation for six weeks and the other was fed normal, unsupplemented feed (control). Each mouse in the test group was fed a daily oral dose of L-carnitine of about 50 mg/kg of body weight. The average daily food for each mouse was determined by weighing the food initially placed in the food bin and weighing the remaining food. The feed was supplemented with L-carnitine so that each mouse in the test group consumed the test dose (50 mg/kg) of L-carnitine each day. Mouse blood was sampled prior to beginning of the trial (pretreatment), at the end of three weeks, and at six weeks (posttreatment), and was evaluated for serum osteocalcin and carnitine levels. The results of this determination are shown in Table 1A below.

Similar tests were performed on six young mice, i.e., 2 months 5 months of age. One group (n=3) was fed a diet with L-carnitine supplementation for three months, the other (n=3) was fed normal, unsupplemented feed (control). Each mouse in the test group was fed a daily oral dose of L-carnitine of about 50 mg/kg of body weight. Mouse blood was sampled prior to beginning of the trial (pretreatment) i.e., at two months of age, and at 5 months of age, and was evaluated for serum osteocalcin and carnitine levels. The results of this determination are shown in Table 1B below.

TABLE 1

Effect of Oral L-Carnitine on Serum Carnitine and Osteocalcin Levels in Aged and Young Mice

| Animals | Serum Carnitine, $\mu M$ | | | Age | ng/ml Osteocalcin |
|---|---|---|---|---|---|
| | Total | Free | Esterified | | |
| A. Aged Mice (18 months old) | | | | | |
| CONTROL (no carnitine) | 56.1 ± 7.9 | 36.6 ± 4.7 | 19.5 ± 5.4 | | 21.3 ± 2.8 |
| CARNITINE TREATED 50 mg/kg/day | 80.2 ± 9.5 | 57.0 ± 9.7 | 23.2 ± 5.6 | | 29.6 ± 3.6 |
| B. Young Mice (2 months-5 months old) | | | | | |
| CONTROL (no carnitine) | 46.2 | 34.8 | 11.7 | 2 mos. 5 mos. | 400 150 |
| CARNITINE TREATED 50 mg/kg/day | 84.2 | 60.2 | 24.3 | 2 mos. 5 mos. | 400 256 |

The data of Table 1A indicate that L-carnitine, at a constant daily dosage of 50 mg per kg of body weight, is effective at increasing serum osteocalcin in aged mice. The measured difference in osteocalcin levels between the treated group and the control group was significant at the $p \leq 0.05$ level using the student's t test. The increased level of osteocalcin is indicative of increased osteoblastic activity, hence, increased bone formation. It is also noted that the test group showed higher carnitine levels than the control group.

The data of Table 1B indicate that, in young mice., the treated group maintained a higher level of osteocalcin at five months, again, indicating increased bone formation activity.

EXAMPLE 2

Comparative Effects of L-Carnitine, Acetyl Carnitine, and γ-Butyrobetaine on Serum Osteocalcin Levels in Mice Tests were performed to compare the effects on serum osteocalcin of diet supplementation with L-carnitine, its precursor, γ-butyrobetaine (available from Aldrich Chemical Co.) and one of its metabolites, acetylcarnitine (available from Life Science Resources, Milwaukee, Wis. 53223). Twenty adult mice, i.e., three months of age, (BALB/c male mice) were divided into seven groups. Each of the groups was fed diets as indicated hereinbelow for twelve weeks. One group (n=3) was fed a diet with L-carnitine supplementation at a dose of 50 mg/kg of body weight each day, while the second group (n=3) was fed L-carnitine at a daily dose of about 100 mg/kg. The third group (n=2) was fed a diet with acetylcarnitine supplementation at a daily dose of 50 mg/kg, while the fourth group (n=3) was fed a daily dose of 100 mg/kg of this compound. The fifth group (n=2) was fed a daily dose of 50 mg/kg of γ-butyrobetaine supplementation, while the sixth group was fed a daily dose of 100 mg/kg of γ-butyrobetaine. The seventh group (n=4) was fed normal, unsupplemented feed (control). Mouse blood was sampled prior to beginning of the trial (pretreatment), at six weeks, and at the end of the trial (twelve weeks). The samples were evaluated for serum osteocalcin levels at six and twelve weeks. Total carnitine was determined at twelve weeks. The results of this determination are shown in Table 2 below.

TABLE 2

Comparison of L-Carnitine, Acetyl Carnitine and γ-Butyrobetaine

| GROUP | TREATMENT | DOSE/DAY | OSTEOCALCIN (ng/ml) 6 wks | OSTEOCALCIN (ng/ml) 12 wks | SERUM CARNITINE ($\mu$M) 12 wks only Total | SERUM CARNITINE ($\mu$M) 12 wks only Free |
|---|---|---|---|---|---|---|
| 001 | L-CARNITINE | 50 mg/kg* | 151 | 153 | 66.0 | 52.1 |
| 002 | L-CARNITINE | 100 mg/kg | 199 | 115 | 59.5 | 41.6 |
| 003 | ACETYL L-CARNITINE | 50 mg/kg | 70 | 62 | 59.6 | 45.6 |
| 004 | ACETYL L-CARNITINE | 100 mg/kg | 60 | 77 | 65.1 | 52.1 |
| 005 | γ-BUTYROBETAINE | 50 mg/kg | 184 | 173 | 63.2 | 40.7 |
| 006 | γ-BUTYROBETAINE | 100 mg/kg | 220 | 122 | 58.5 | 40.4 |
| 007 | CONTROL | — | 124 | 96 | 45.2 | 32.9 |

*It is noted that the actual amount of carnitine and derivatives consumed by each mouse was estimated at only about half the indicated values especially at the higher dosage level where the feed had a more pronounced taste from the carnitine compounds. The measured difference in osteocalcin levels between the goups treated with L-carnitine and with γ-butyrobetaine and the control group appear to be significant at the following levels using the student's t test: L-carnitine (50 mg) v. control at $p < 0.01$; L-carnitine (100 mg) v. control at $p < 0.05$; γ-butyrate betaine (50 mg) v. control at $p < 0.05$; γ-butyrobetaine (100 mg) v. control at $p < .01$. For acetyl carnitine treatment, the osteocalcin of the control v. acetyl L-carnitine (50 mg) was significantly higher for the control at the $p < 0.01$ level; acetyl L-carnitine (100 mg) v. control showed no significant difference.

The data of Table 2 indicate that γ-butyrobetaine and L-carnitine stimulate osteocalcin production in adult mice (5–6 months of age). Serum osteocalcin at six weeks increased in a dose dependent manner (50 vs. 100 mg/kg/day) in L-carnitine (151±4 vs. 199±7 ng/ml) and in γ-butyrobetaine (184±6 vs. 220±75 ng/ml). Only L-carnitine- and γ-butyrobetaine-treated mice maintained osteocalcin blood levels. These data indicate that γ-butyrobetaine, the direct biological precursor of carnitine biosynthesis, is at least as effective as, and possibly better than, L-carnitine in increasing osteocalcin levels. On the other hand, acetylcarnitine appeared to have an inhibitory effect on osteocalcin production (70±4 vs. 61±6 ng/ml), i.e., acetyl carnitine-treated mice showed a decrease in serum osteocalcin.

HUMAN STUDIES

EXAMPLE 3

Carnitine levels in healthy human adults of the age of 60

Thirty-eight healthy adults over the age of 60 were enrolled in an open label study. Blood of the selected patients was sampled and serum carnitine levels, total, free and esterified, were determined. The results of the determinations are given in Table 3.

TABLE 3

Serum Carnitine Levels in 40 Randomly Selected Adults 60 or Over Years Old

| Subject | Carnitine $\mu$M Total | Free | Esters | Esterified/ Free |
|---|---|---|---|---|
| 001 | 65.7 | 49.2 | 16.5 | 0.34 |
| 002 | 67.9 | 57.8 | 10.1 | 0.17 |
| 003 | 62.9 | 48.6 | 14.3 | 0.29 |
| 004 | 51.1 | 39.2 | 11.9 | 0.30 |
| 005 | 51.1 | 45.8 | 5.3 | 0.12 |
| 006 | 46.1 | 32.6 | 13.5 | 0.41 |
| 007 | 93.5 | 79.8 | 13.7 | 0.17 |
| 008 | 64.3 | 50.4 | 13.9 | 0.28 |
| 009 | 49.2 | 42.0 | 7.2 | 0.17 |
| 010 | 57.0 | 52.4 | 4.6 | 0.09 |
| 011 | 49.2 | 34.2 | 15.0 | 0.44 |
| 012 | 58.4 | 53.0 | 5.4 | 0.10 |
| 013 | 53.8 | 46.6 | 7.2 | 0.15 |
| 014 | 63.8 | 47.8 | 16.0 | 0.33 |
| 015 | 45.6 | 42.6 | 3.0 | 0.07 |
| 016 | 58.4 | 46.8 | 11.6 | 0.25 |
| 017 | 80.7 | 59.2 | 21.5 | 0.36 |
| 018 | 54.7 | 46.8 | 7.9 | 0.17 |
| 019 | 50.2 | 36.8 | 13.4 | 0.36 |
| 020 | 61.1 | 55.0 | 6.1 | 0.11 |
| 021 | 60.6 | 44.0 | 16.6 | 0.38 |
| 022 | 38.8 | 38.0 | 0.8 | 0.02 |
| 023 | 52.9 | 49.4 | 3.5 | 0.07 |
| 024 | 51.5 | 44.2 | 7.3 | 0.17 |
| 025 | 43.3 | 38.8 | 4.5 | 0.12 |
| 026 | 53.4 | 37.6 | 15.8 | 0.42 |
| 027 | 67.5 | 56.6 | 10.9 | 0.19 |
| 028 | 46.5 | 34.2 | 12.3 | 0.36 |
| 029 | 79.8 | 56.6 | 23.2 | 0.41 |
| 030 | 60.2 | 38.8 | 21.4 | 0.55 |
| 031 | 42.0 | 35.0 | 7.0 | 0.20 |
| 032 | 67.5 | 42.0 | 25.5 | 0.61 |
| 033 | 61.6 | 51.4 | 10.2 | 0.20 |
| 034 | 51.1 | 36.8 | 14.3 | 0.39 |

TABLE 3-continued

Serum Carnitine Levels in
40 Randomly Selected Adults
60 or Over Years Old
Carnitine
μM

| Subject | Total | Free | Esters | Esterified/Free |
|---|---|---|---|---|
| 035 | 72.0 | 55.0 | 17.0 | 0.31 |
| 036 | 59.7 | 44.0 | 15.7 | 0.36 |
| 037 | 40.1 | 34.6 | 5.5 | 0.16 |
| 038 | 44.7 | 30.8 | 13.9 | 0.45 |
| 039 | 55.6 | 45.0 | 10.6 | 0.24 |
| 040 | 47.4 | 35.0 | 12.4 | 0.35 |

Seven of these patients showed serum carnitine insufficiency, i.e., on E/F≧0.4 (Winter et al., *Am. J. Diseases Child.*, vol. 141 (1987) pp. 660). However, 50% (20) of the patients were found to have an E/F above 0.25. It has been found in determinations in the inventor's laboratory of well over 10,000 patients that an E/F at or above 0.25 indicates elevated carnitine esters and suggests abnormal carnitine metabolism. (See, "Normal Carnitine Levels in Body Fluids and Tissues," Metabolic Analysis Labs, Inc., Madison, Wis.) Because carnitine esters are rapidly excreted in the urine, elevated serum esters can lead to an increased demand for free carnitine, which may not be supplied by the diet or increased synthesis in the aged adult. The finding that 50% of randomly selected aged patients have an E/F greater than 0.25 suggests that many aged patients might have an increased requirement for free carnitine, and that treatment with oral carnitine could stimulate the in vivo synthesis of IGF-1 and osteocalcin, and in turn, could lead to increased body levels of the growth hormone and bone formation. The following examples show the results of such carnitine supplementation.

EXAMPLE 4

IGF-1 Response to L-Carnitine Supplementation in Healthy Human Adults Over Age 60

Seven adults from Example 3 agreed to receive a daily dosage of L-carnitine of 2 g/day, self-administered orally, for three months. Doses were administered four times daily, and each dose consisted of two 250 mg tablets. Of the seven individuals, two individuals dropped out of the study due to unrelated illness; thus, five remained in the study to completion. The following were evaluated by pretreatment and posttreatment comparisons: serum carnitine and serum IGF-1 by known methods, and bone mineral contents by bone scan of thoracic region, i.e., thoracic vertebrae, on a NORLAND scanner. The results of these determinations are given in Tables 4A and 4B below.

TABLE 4A

Effect of Oral Carnitine Treatment on Serum Carnitine and IGF-1 Levels

| | IGF-1, ng/ml | |
|---|---|---|
| SUBJECT | PRETREATMENT | POSTTREATMENT |
| 001 | 140 | 396 |
| 002 | 208 | 280 |
| 003 | 120 | 148 |
| 004 | 238 | 270 |
| 005 | 144 | 264 |

CARNITINE μM

| | PRETREATMENT | | | | POSTTREATMENT | | | |
|---|---|---|---|---|---|---|---|---|
| SUBJ. | TOTAL | FREE | ESTER | E/F | TOTAL | FREE | ESTER | E/F |
| 001 | 64.8 | 48.4 | 16.4 | 0.34 | 101.7 | 77.2 | 24.5 | 0.32 |
| 002 | 58.8 | 43.6 | 15.2 | 0.35 | 70.7 | 57.0 | 13.7 | 0.24 |
| 003 | 43.8 | 35.4 | 8.4 | 0.24 | 68.9 | 55.4 | 13.5 | 0.24 |
| 004 | 33.7 | 24.4 | 9.3 | 0.38 | 54.7 | 38.6 | 16.1 | 0.42 |
| 005 | 51.5 | 39.8 | 11.7 | 0.29 | 73.4 | 44.8 | 28.6 | 0.64 |

The data of Table 4A indicate that total carnitine and IGF-1 increased. The mean change in IGF-1 was 170 to 272 ng/ml. Using a Wicoxon test of paired comparisons, this increase was significant at $p \leq 0.05$.

TABLE 4B

Effect of Oral Carnitine Treatment on Bone Mineral Content in Aged Patients

| | BONE MINERAL CONTENT, g | | |
|---|---|---|---|
| SUBJECT | PRE TREATMENT | POST TREATMENT | CHANGE |
| 001 | 461.7 | 427.0 | +3.85% |
| 002 | 1076.9 | 1118.4 | +1.39% |
| 003 | 933.0 | 986.1 | +5.69% |
| 004 | 730.4 | 736.2 | +0.72% |
| 005 | 827.8 | 887.7 | +7.35% |

The data of Table 4B indicate that all patients demonstrated an increase in bone mineral content of the thoracic vertebral region after treatment with L-carnitine. This body region is considered a key area for bone health in aged patients.

EXAMPLE 5

Effects of Oral L-carnitine Treatment on Serum Levels of IGF-1 and Carnitine in Patients Over Age 60

Nineteen patients (over age 60) were enrolled in a preliminary double-blind study to establish the effect of oral L-carnitine treatment on serum IGF-1 and osteocalcin levels. Baseline, i.e., pretreatment, levels of serum IGF-1, osteocalcin and carnitine were measured by known methods. The patients were divided into two groups, control (n=9; subjects 001–009 in Table 5 below) and treatment (n=10; subjects 010–019 in Table 5 below). The treatment group received a daily dosage of 2 g of L-carnitine orally, self-administered, in four separate doses of two 250 mg tablets taken four times per day, for twelve weeks. The control group were given placebo, e.g., simple sugar. Serum samples were drawn every four weeks, and serum carnitine, IGF-1 and osteocalcin were determined. The results of the determinations are given in Table 5.

TABLE 5

Effects of Oral L-Carnitine Treatment on Serum Carnitine in Aged Patients

| | L-CARNITINE | | | | | | | |
|---|---|---|---|---|---|---|---|---|
| | μM | | IGF-1 | OSTEO-CALCIN | μM | | IGF-1 | OSTEO-CALCIN |
| SUBJ. | TOTAL | FREE | ng/ml | ng/ml | TOTAL | FREE | ng/ml | ng/ml |
| | PRETREATMENT | | | | 4 WEEKS | | | |
| 001 | 57.5 | 51.4 | 226 | 11.0 | 54.3 | 47.2 | 246 | 10.1 |
| 002 | 64.8 | 49.8 | 181 | 13.7 | 64.3 | 49.8 | 242 | 12.0 |
| 003 | 51.5 | 40.4 | 177 | 8.0 | 48.8 | 34.2 | 136 | 10.7 |
| 004 | 46.5 | 38.2 | 247 | 7.6 | 52.9 | 45.0 | 228 | 9.5 |
| 005 | 50.6 | 43.6 | 196 | 14.3 | 43.3 | 39.8 | 148 | 14.4 |
| 006 | 48.8 | 35.6 | 103 | 3.5 | 51.1 | 35.6 | 105 | 4.6 |
| 007 | 44.2 | 37.8 | 247 | 7.6 | 47.9 | 34.6 | 219 | 6.8 |
| 008 | 50.6 | 40.2 | 175 | 4.9 | 48.3 | 39.0 | 126 | 1.8 |
| 009 | 51.1 | 42.2 | 143 | 7.7 | 52.9 | 44.8 | 180 | 9.2 |
| 010 | 49.7 | 38.0 | 79 | 10.7 | 71.6 | 54.4 | 118 | 11.8 |
| 011 | 46.5 | 39.6 | 180 | 12.1 | 72.5 | 61.6 | 192 | 13.6 |
| 012 | 49.7 | 35.0 | 206 | 7.6 | 52.4 | 36.6 | 62 | 7.4 |
| 013 | 56.5 | 50.4 | 182 | 10.1 | 80.3 | 66.6 | 213 | 11.5 |
| 014 | 83.0 | 58.8 | 272 | 6.3 | 119.9 | 67.4 | 305 | 7.9 |
| 015 | 34.2 | 24.6 | 274 | 9.0 | 67.0 | 52.0 | 318 | 10.4 |
| 016 | 71.1 | 51.4 | 163 | 10.2 | 84.4 | 67.2 | 185 | 11.6 |
| 017 | 30.1 | 24.6 | 127 | 3.5 | 54.3 | 40.4 | 178 | 3.6 |
| 018 | 62.0 | 49.8 | 241 | 5.9 | 73.0 | 61.2 | 244 | 7.9 |
| 019 | 72.5 | 58.2 | 234 | 5.1 | 108.5 | 85.0 | 173 | 5.9 |
| | 8 WEEKS | | | | 12 WEEKS | | | |
| 001 | 51.1 | 44.2 | 226 | 11.7 | 54.7 | 46.4 | 190 | 11.1 |
| 002 | 61.1 | 55.2 | 244 | 9.8 | 51.1 | 46.8 | 174 | 11.7 |
| 003 | — | — | — | — | — | — | — | — |
| 004 | 51.1 | 39.0 | 192 | 8.0 | 52.9 | 44.0 | 178 | 6.1 |
| 005 | — | — | — | — | — | — | — | — |
| 006 | 46.9 | 40.2 | 126 | 4.2 | 57.0 | 42.4 | 108 | 3.0 |
| 007 | 49.2 | 35.6 | 164 | 8.0 | 49.7 | 38.4 | 176 | 8.5 |
| 008 | 47.9 | 37.6 | 101 | 0.5 | 53.8 | 39.0 | 188 | 2.9 |
| 009 | 52.9 | 45.0 | 231 | 12.2 | 58.4 | 48.4 | 172 | 8.3 |
| 010 | 88.0 | 65.4 | 147 | 11.9 | 100.8 | 72.6 | 108 | 9.3 |
| 011 | 76.6 | 58.6 | 197 | 10.2 | 79.3 | 61.0 | 157 | 11.8 |
| 012 | 64.8 | 52.6 | 248 | 7.0 | 62.0 | 49.6 | 179 | 8.7 |
| 013 | 72.5 | 65.2 | 197 | 10.8 | — | — | — | — |
| 014 | 91.7 | 74.6 | 157 | — | 75.7 | 70.0 | 260 | 7.0 |
| 015 | 67.9 | 57.0 | 329 | 9.0 | 70.2 | 55.8 | 260 | 9.1 |
| 016 | 83.4 | 67.4 | 201 | 11.0 | 94.4 | 69.6 | 185 | 11.4 |
| 017 | 51.5 | 39.4 | 163 | 2.4 | — | — | — | — |
| 018 | — | — | — | — | — | — | — | — |
| 019 | 83.9 | 61.2 | 168 | 4.9 | 88.0 | 70.0 | 207 | 6.5 |

The average pretreatment total carnitine levels for the control group and the treatment group were 51.7 μM and 55 μM, respectively. There was no statistically significant difference between these baseline values. At four weeks, the averages were 51.5 μM (control) and 78.4 μM (treatment); at eight weeks, 51.5 μM (control) and 75.6 μM (treatment); and at twelve weeks, 51.5 μM (control) and 81.5 μM (treatment). Using a two-factor repeated measure Anova analysis, the total serum carnitine was significantly higher in the treatment group at the p=0.0013 level.

The average pretreatment serum IGF-1 levels for the control group and the treatment group were 188.3 ng/ml and 195.8 ng/ml, respectively. At four weeks, the averages were 181.1 ng/ml (control) and 214.0 ng/ml (treatment); at eight weeks, 181 ng/ml (control) and 200.8 ng/ml (treatment); and at twelve weeks, 169.4 ng/ml (control) and 193.7 ng/ml (treatment). At the four weeks mark, using a Mann-Whitney test for change in IGF-1, IGF-1 was significantly higher in the carnitine treatment group at p=0.03. The average serum IGF-1 was higher at eight weeks and twelve weeks, but, because of a decrease in patient number, the differences were just below significance. In general, however, it can be seen that IGF-1 levels decreased in the control group and increased in the carnitine treatment group.

The average pretreatment serum osteocalcin levels for the control group and the treatment group were 8.7 ng/ml and 8.1 ng/ml, respectively. At four weeks, the averages were 8.8 ng/ml (control) and 9.2 ng/ml (treatment); at eight weeks, 7.8 ng/ml (control) and 8.4 ng/ml (treatment); and at twelve weeks, 7.4 ng/ml (control) and 9.1 ng/ml (treatment). It is seen the average serum osteocalcin increased in the treatment group at each determination level of the study, while the average serum osteocalcin of the control group decreased. These differences were just below significance. It is thought that this is due to the fact that all patients pretreatment had osteocalcin levels in the high normal range and the test sample of the study wa too small.

As shown, however, in FIG. 1, greater effects from carnitine treatment are shown when pretreatment values of osteocalcin are low or below normal. There appears to be a relationship between pretreatment (baseline) IGF-1 (if under 200 ng/ml) and the amount of increase in IFG-1. There were five patients in the study with pretreatment IGF-1 under 200 ng/ml who received carnitine. For these five, the correlation between pretreatment IGF-1 and increase in IGF-1 at the four week period was −0.654. Thus, the lower the baseline level of IGF-1, the greater the increase in IGF-1 with carnitine treatment.

It should be appreciated that in the Rudman et al. study described hereinbefore, patients were selected with below normal levels of IGF-1 (i.e., less than 350 U/L). In this study, patients were randomly selected, and as a result only one patient (subject 010) had a below normal pretreatment IGF-1 level (baseline) of 329 U/L. All other patients had serum IGF-1 and serum osteocalcin levels within the normal range. Nevertheless, it is important to note that after treatment with L-carnitine, the serum IGF-1 increased and remained above 500 U/L (a normal level) at the four, eight and twelve week intervals. Thus, L-carnitine treatment restored and maintained IGF-1 levels at the normal range for the entire twelve week test period.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A method for preventing reduced serum insulin-like growth factor (IGF-1) concentration in a patient predisposed to or suffering from a reduced IGF-1 concentration, comprising administering to said patient an amount effective to increase or maintain serum IFG-1 concentration of a compound of formula (I):

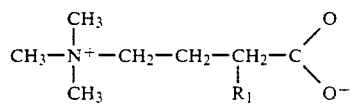

wherein $R_1$ is hydrogen or hydroxyl.

2. The method of claim 1, wherein said effective amount is a daily dose of about 1.5 g to about 5 g.

3. The method of claim 1, wherein said effective amount is a daily dose of about 1 g. to about 4 g.

4. The method of claim 2, wherein said daily dose is divided into separate doses administered separately.

5. The method of claim 1, wherein said compound is administered orally.

6. A method for stimulating bone formation in an animal or human being suffering from or predisposed to bone depletion, comprising administering to said animal or human being an effective amount of a compound of formula (I):

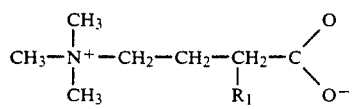

wherein $R_1$ is hydrogen or hydroxyl.

7. A method for stimulating bone formation in an aged animal or human being, comprising administering to said animal or human being an amount effective to increase serum osteocalcin concentration of a compound of formula (I):

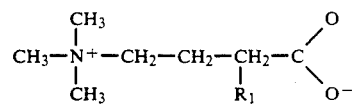

wherein $R_1$ is hydrogen or hydroxyl.

8. The method of claim 1 wherein said amount is in daily dosage about 1 g to about 5 g.

9. The method of claim 7, wherein said compound is L-carnitine.

10. The method of claim 7, wherein said compound is γ-butyrobetaine.

11. A method for increasing bone mineral content in a patient having elevated serum carnitine ester concentration, comprising administering an amount effective to normalize said ester concentration of a compound of formula (I):

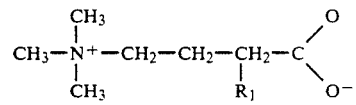

wherein $R_1$ is hydrogen or hydroxyl.

12. A method for stimulating bone formation in a patient suffering from or predisposed to bone depletion, comprising:
  detecting in a patient a ratio of serum esterified carnitine to free carnitine of 0.25 or greater,
  administering to said patient an effective amount of a compound of formula (I):

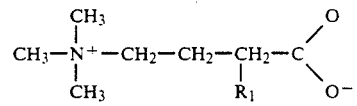

wherein $R_1$ is hydrogen or hydroxyl, to increase serum osteocalcin concentration; and
  continuing said administrating such that bone mineral accumulation is indicated in the skeleton of said patient.

13. A method for preventing bone loss in a patient suffering from or predisposed to bone depletion, comprising administering to a patient suffering therefrom an amount effective to increase serum IGF-1 concentration of a compound of formula (I) :

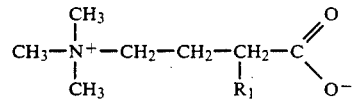

wherein $R_1$ is hydrogen or hydroxyl.

* * * * *

UNITED STATES PATENT AND TRADEMARK OFFICE
CERTIFICATE OF CORRECTION

PATENT NO. : 5,240,961  
DATED : August 31, 1993  
INVENTOR(S) : Shug

Page 1 of 2

It is certified that error appears in the above-indentified patent and that said Letters Patent is hereby corrected as shown below:

Column 12 lines 33-43,

Delete:

"TABLE 4B

Effect of Oral Carnitine Treatment on Bone Mineral Content in Aged Patients

BONE MINERAL CONTENT, g

| SUBJECT | PRE TREATMENT | POST TREATMENT | CHANGE |
|---|---|---|---|
| 001 | 461.7 | 427.0 | +3.85% |
| 002 | 1076.9 | 1118.4 | +1.39% |
| 003 | 933.0 | 986.1 | +5.69% |
| 004 | 730.4 | 736.2 | +0.72% |
| 005 | 827.8 | 887.7 | +7.35% |

".

UNITED STATES PATENT AND TRADEMARK OFFICE
CERTIFICATE OF CORRECTION

PATENT NO. : 5,240,961
DATED : August 31, 1993
INVENTOR(S) : Shug

It is certified that error appears in the above-indentified patent and that said Letters Patent is hereby corrected as shown below:

And insert:

--TABLE 4B
Effect of Oral Carnitine Treatment on
Bone Mineral Content in Aged Patients

| | BONE MINERAL CONTENT, g | | |
|---|---|---|---|
| SUBJECT | PRE TREATMENT | POST TREATMENT | CHANGE |
| 001 | 1076.9 | 1118.4 | +3.85% |
| 002 | 1173.7 | 1190.0 | +1.39% |
| 003 | 933.0 | 986.1 | +5.69% |
| 004 | 730.9 | 736.2 | +0.72% |
| 005 | 827.5 | 888.3 | +7.35% |

--.

Signed and Sealed this

Thirtieth Day of August, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,240,961
DATED : August 31, 1993
INVENTOR(S) : Austin L. Shug

It is certified that error appears in the above-indentified patent and that said Letters Patent is hereby corrected as shown below:

Column 5, formula (I), that portion of the formula reading

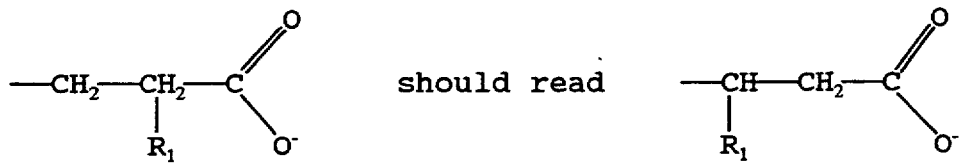

Column 15, formula (I), lines 33-37, 53-57, and column 16 lines 5-9, 23-27, 37-42 for each occurrence of formula (I) that portion of the formula reading

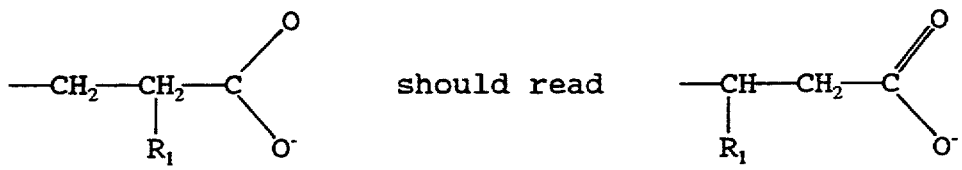

UNITED STATES PATENT AND TRADEMARK OFFICE
CERTIFICATE OF CORRECTION

PATENT NO. : 5,240,961
DATED : August 31, 1993
INVENTOR(S) : Austin L. Shug

It is certified that error appears in the above-indentified patent and that said Letters Patent is hereby corrected as shown below:

Column 16, lines 54-58 for formula (I), that portion of the formula reading

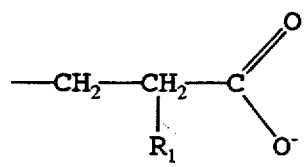   should read   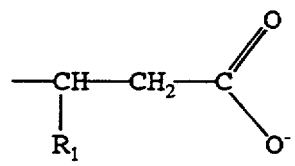

Signed and Sealed this

Twentieth Day of June, 1995

Attest:

BRUCE LEHMAN

*Attesting Officer*      *Commissioner of Patents and Trademarks*